United States Patent [19]
Wythes et al.

[11] Patent Number: 5,945,118
[45] Date of Patent: Aug. 31, 1999

[54] INDOLE DERIVATIVE FOR THE TREATMENT OF MIGRAINE

[75] Inventors: Martin James Wythes; Paul Morgan, both of Sandwich, United Kingdom

[73] Assignee: Pfizer Inc, New York, N.Y.

[21] Appl. No.: 08/946,493

[22] Filed: Oct. 7, 1997

Related U.S. Application Data

[63] Continuation of application No. PCT/EP95/03885, Sep. 29, 1995.

[51] Int. Cl.⁶ ............................... A61L 9/04; A61F 2/02; A61K 9/20; A61K 9/48
[52] U.S. Cl. ............................ 424/434; 424/44; 424/45; 424/423; 424/435; 424/436; 424/451; 424/464
[58] Field of Search ................................. 424/44, 45, 423, 424/451, 464, 434, 435, 436

[56] References Cited

FOREIGN PATENT DOCUMENTS

WO9206973  4/1992  WIPO .
WO9425023  11/1994  WIPO .

*Primary Examiner*—Carlos A. Azpuru
*Attorney, Agent, or Firm*—P. C. Richardson; P. H. Ginsburg; J. W. Appleman

[57] ABSTRACT

This invention relates to (R)-5-(aminosulphonylmethyl)-3-(N-methylpyrrolidin-2-ylmethyl)-1H-indole and its pharmaceutically acceptable salts. This compound is particularly useful in treating disorders arising from deficient serotonergic neurotransmission, especially migraine.

14 Claims, No Drawings

INDOLE DERIVATIVE FOR THE TREATMENT OF MIGRAINE

This is a continuation of International Patent Application Serial No. PCT/EP95/03885, filed Sep. 29, 1995, which published as WO 96/11923, on Apr. 25, 1996, which is a continuation of Great Britain Patent Applications 9611401.3, filed Jun. 6, 1995, and 9520529.1, filed Oct. 12, 1994.

This invention relates to an indole derivative useful in the treatment or prophylaxis of certain medical disorders.

More particularly, the invention relates to the compound (R)-5-(aminosulphonylmethyl)-3-(N-methylpyrrolidin-2-ylmethyl)-1H-indole of the formula:

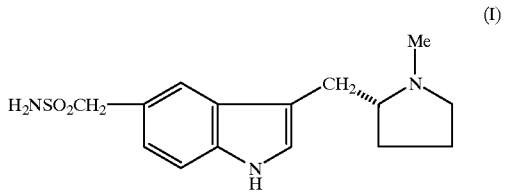

and its pharmaceutically acceptable salts.

The compound (I) is disclosed generically but not specifically in WO-A-92/06973. It is specifically disclosed in British patent application no. 9420529.1 filed on Oct. 12, 1994. British patent application no. 9424471.2 filed on Dec. 3, 1994 also discloses the use of this compound in treating emesis.

The compound (I) and its pharmaceutically acceptable salts are potent serotonin ($5-HT_1$) agonists which, according to WO-A-92/06973, can be used in the treatment of disorders arising from deficient serotonergic neurotransmission such as depression, anxiety, eating disorders, obesity, drug abuse, cluster headache, migraine, pain, chronic paroxysmal hemicrania, and headache associated with vascular disorders. The compound (I) is also useful for the new utilities described in British patent application nos. 9420529.1 and 9424471.2.

WO-A-94/25023 published on Nov. 10, 1994, Brain Research, 628 (1993), 303–305 and Society for Neuroscience Abstracts, Vol. 19, Part 2, 23rd Annual meeting, Washington D.C., Nov. 7th–12th, 1993, Abstract no. 565.6, describe the enhanced potency of (R)-5-(methylaminosulfonyl-methyl)-3-(N-methylpyrrolidin-2-ylmethyl)-1H-indole and (R)-5-(methylaminosulfonylmethyl)-3-(pyrrolidin-2-ylmethyl)-1H-indole.

The compound of the formula (I) and its salts are also unexpectedly potent and active at doses less than those disclosed in WO-A-92/06973.

Thus in one aspect the invention provides (R)-5-(aminosulphonylmethyl)-3-(N-methylpyrrolidin-2-yl)-1H-indole and its pharmaceutically acceptable salts.

Preferably the compound (I) is in pure, isolated form (i.e. synthetically produced).

The compound (I) can be prepared conventionally, e.g. by the techniques described in WO-A-92/06973, but can also be prepared in unexpectedly good yield by the process described in the following Preparations and Example, which utilise the Mitsunobu coupling reaction.

The compound of the present invention is basic in nature and is capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compound of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as the hydrochloride, hydro-bromide, hydroiodide, nitrate, sulfate or bisulfate, phosphate or acid phosphate, acetate, lactate, citrate or acid citrate, tartrate or bitartrate, succinate, maleate, fumurate, gluconate, saccharate, benzoate, methanesulfonate and pamoate [i.e., 1,1'-methylene-bis-(2-hydroxy-3-naphthoate)] salts.

The compound of the invention is evaluated as an antimigraine agent by testing the extent to which it mimics sumatriptan in contracting the dog isolated saphenous vein strip (P. P. A. Humphrey et al., *Br. J. Pharmacol.*, 94, 1128 (1988)). This effect can be blocked by methiothepin, a known serotonin antagonist. Sumatriptan is known to be useful in the treatment of migraine and produces a selective increase in carotid vascular resistance in the anaesthetised dog. It has been suggested (W. Fenwick et al., *Br. J. Pharmacol.*, 96, 83 (1989)) that this is the basis of its efficacy.

The compound of the present invention can also be evaluated as an anti-migraine agent via the plasma protein extravasation response within the dura mater of guinea pigs following unilateral electrical trigeminal ganglion stimulation. The extent to which they mimic sumatriptan, in terms of both potency and efficacy, is determined in this assay. The procedure is performed on male Hartley guinea pigs (200–250 g, Charles River Laboratories, Wilmington, Ma., U.S.A.) as described in Markowitz et al., *J. Neurosci.*, 7 (12), 4129–4136 (1987). The procedure briefly consists of placing pentobarbitone-anaesthetized animals in a stereotaxic frame. $^{125}$I-BSA (bovine serum albumin) ($50 \mu Ci/kg^1$) is first injected into the femoral vein, followed by 5 minutes later by drug or vehicle. Bipolar electrodes are then lowered into the trigeminal ganglia, and the right ganglion is stimulated for 5 minutes (1.2 nA, 5 Hz, 5 msec). The animal is then perfused with saline through the left cardiac ventricle and sacrificed, and the dura mater is dissected, weighed, and counted for radioactivity. Cpm/mg wet weight values are determined for the right vs left dura mater, and a ratio for the stimulated vs unstimulated sides is generated for each animal. Unpaired student's t-test is used to statistically compare these ratio values in respective groups treated with vehicle or drug. The M.E.D. (minimally effective dose) for a given compound is the lowest dose for which the mean value of this ratio is significantly lower than that obtained for the vehicle-treated group. The effect of the drugs in these assays can be partially blocked by metergoline, a known serotonin antagonist.

A similar procedure to the one described above can be performed on rats, as described in Matsubara, et. al., *Br. J. Pharmacol.*, 104, 3 (1991).

Pharmaceutical compositions containing the compound of the present invention can be formulated in a conventional manner using one or more pharmaceutically acceptable carriers. Thus, the active compounds of the invention may be formulated for oral, sublingual, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxy-benzoates or sorbic acid).

For sublingual and buccal administration the composition can take the form of tablets or lozenges formulated in conventional manner.

The compound of the invention can be formulated for parenteral administration by injection, including using conventional catheterization techniques or infusion. Formulations for injection may be presented in unit dosage form e.g. in ampules or in multi-dose containers, with an added preservative. The compositions may take such forms as suspensions, solutions or emulsions in oily or aqueous vehicles, and may contain formulating agents such as suspending, stabilising and/or dispersing agents. Alternatively, the active ingredient may be in powder form for reconstitution with a suitable vehicle, e.g. sterila pyrogen-free water, before use.

The compound of the invention can also be formulated in rectal compositions such as suppositories or retention enemas, e.g., containing conventional suppository bases such as cocoa butter or other glycerides.

For intranasal administration or administration by inhalation, the compound of the invention is conveniently delivered in the form of a solution or suspension from a pump spray container that is squeezed or pumped by the patient or as an aerosol spray presentation from a pressurised container or a nebulizer, with the use of a suitable propellant, e.g. dichlorodifluoromethane, trichlorofluoromethane, dichlorotetrafluoroethane, carbon dioxide or other suitable gas. In the case of a pressurised aerosol, the dosage unit may be determined by providing a valve to deliver a metered amount. The pressurised container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

As stated previously, the compound (I) and its salts are exceptionally active and are also useful at doses much lower than those described in WO-A-92/06973.

Thus a suitable dose of the compound (R)-5-(aminosulfonyl-methyl)-3-(N-methylpyrrolidin-2-ylmethyl)-1H-indole or its pharmaceutically acceptable salts for oral, parenteral or buccal administration to the average adult human for the treatment of the conditions referred to above (e.g., migraine) is 0.1 $\mu$g to 200 mg of the compound or salt thereof per unit dose which could be administered, for example, 1 to 4 times per day. In one embodiment, the pharmaceutical composition includes 0.1 $\mu$g to less than 0.1 mg of the compound or salt thereof per unit dose. In another embodiment, the pharmaceutical composition includes 0.1 $\mu$g to 0.09 mg of the compound or salt thereof per unit dose, and, in still another embodiment, the pharmaceutical composition includes 0.5 $\mu$g to 0.09 mg of the active ingredient per unit dose.

Aerosol formulations for treatment of the conditions referred to above (e.g. migraine) in the average adult human are preferably arranged so that each metered dose or "puff" of aerosol contains 0.01 $\mu$g to 1000 $\mu$g of the compound (R)-5-(aminosulfonylmethyl)-3-(N-methyl-pyrrolidin-2-ylmethyl)-1H-indole or a pharmaceutically acceptable salt thereof. In one embodiment, each metered dose or "puff" of aerosol contains 0.01 $\mu$g to less than 20 $\mu$g of the compound or salt thereof, and, in another embodiment, each metered dose or "puff" of aerosol contains 0.01 $\mu$g to 19 $\mu$g of the active ingredient, and in a still further embodiment, each metered dose or "puff" of aerosol contains 0.05 $\mu$g to 19 $\mu$g of the active ingredient. The overall daily dose with an aerosol will be within the range of 0.05 $\mu$g to 10 mg. In one embodiment, the overall daily dose with an aerosol will be within the range 0.05 $\mu$g to less than 100 $\mu$g of the compound or salt thereof, and, in another embodiment, the overall daily dose with an aerosol will be within the range 0.05 $\mu$g to 99 $\mu$g of the compound. Administration may be several times daily, for example 2,3,4 or 8 times, giving for example, 1,2 or 3 doses each time.

The following Preparations and Example illustrate the preparation of the compound of the present invention. Melting points are uncorrected. NMR data are reported in parts per million ($\delta$) and are referenced to the deuterium lock signal from the sample solvent. Specific rotations were measured at room temperature using the sodium D line (589 nm).

Commercial reagents were utilised without further purification. Chromatography refers to column chromatography performed using 32–63 $\mu$m silica gel and executed under nitrogen pressure (flash chromatography) conditions. Room temperature refers to 20–25° C.

Preparation 1

4-(Nitrophenyl)methanesulphonyl chloride

To a stirred solution of sodium thiosulphate (72.0 g, 0.291 mol) in water (75 mL) and methanol (50 mL) was added at room temperature, over 5 minutes, 4-nitrobenzyl chloride (50.0 g, 0.291 mol). The resulting reaction mixture was heated to reflux and stirred, at reflux, for a further 2.25 hours. The reaction mixture was then cooled down and evaporated under reduced pressure, azeotroping with toluene to give a white solid (150 g). The white solid was added to a mixture of acetic acid (75 mL), water (100 mL) and ice, the reaction mixture cooled to 0° C. and chlorine gas passed through the system for 1.25 hours, maintaining the reaction temperature below 10° C. throughout. The excess chlorine gas was removed by purging the reaction mixture with nitrogen gas for 1.25 hours. The resulting slurry was filtered, drying the solid thus obtained in air. The title compound thus obtained (60.5 g) was used as such in Preparation 2 without further purification or characterisation.

Preparation 2

4-t-Butylaminosulphonylmethylnitrobenzene

To a cooled (ice bath) solution of t-butylamine (48.45 mL, 461 mmol) in dichloromethane (500 ml) was added dropwise, with stirring, a solution of the product of Preparation 1 (54.33 g, 231 mmol) in dichloromethane (500 mL). This addition was carried out over 15 minutes with the temperature maintained below 10° C. throughout. The reaction was then allowed to warm to room temperature and stirred for a further 12 hours. The reaction was then diluted with water (200 mL), the organic layer separated, washed sequentially with water and brine, dried ($MgSO_4$) and evaporated under reduced pressure to give the product as a brown solid. Recrystalization of the brown solid from ethanol gave the title compound as a white solid (49.0 g) : mp, 156–158° C.; TLC (dichloromethane/methanol 30:0.4): Rf=0.66. $^1$H NMR ($CDCl_3$) δ 8.25 (d, 2H), 7.6 (d, 2H), 4.40 (s, 2H), 4.10 (s, 1H), 1.38 (s, 9H). Anal. calcd. for $C_{11}H_{16}N_2O_4S$: C, 48.55; H, 5.97; N, 10.30. Found: C, 48.53; H, 5.92; N, 10.29.

Preparation 3

4-t-Butylaminosulphonylmethylaniline

A solution of the product of Preparation 2 (1.17 g, 4.29 mmol) in absolute ethanol and 10% palladium on carbon (0.32 g) was stirred under a hydrogen atmosphere (60 psi) at 60° C. for 66 hours. The mixture was filtered through CELITE (Trade Mark) filter aid and the resulting solution evaporated under reduced pressure to give the product as a solid. Recrystallization from ethanol gave the title compound as a white solid (0.95 g): mp, 137–138° C.; TLC (dichloromethane/methanol 30:0.4): Rf=0.43. $^1$H NMR ($CDCl_3$) δ 7.20 (d, 2H), 6.65 (d, 2H), 4.15 (s, 2H), 3.95 (br s, 1H), 3.75 (br s, 2H), 1.32 (s, 9H). Anal. calcd. for $C_{11}H_{18}N_2O_2S$: C, 54.51; H, 7.49; N, 11.56. Found: C, 54.76; H, 7.60; N, 11.43.

Preparation 4

4-(t-Butylaminosulphonylmethyl)-2,6-dibromoaniline

To a stirred solution of the product of Preparation 3 (0.77 g, 3.17 mmol) in dichloromethane (15 mL) and methanol (15 mL) was added sodium bicarbonate (0.80 g, 9.53 mmol) with stirring, at 20° C. Bromine (0.315 mL, 6.11 mmol) was then added dropwise to the resultant slurry. The resulting mixture was then stirred for 18 hours, concentrated in vacuo and taken up in ethyl acetate/water (1:1). The aqueous layer was separated and extracted with ethyl acetate. The combined organic layers were then washed with water, dried ($MgSO_4$) and evaporated under reduced pressure to give the product as a white solid. Recrystallization from hexane/ethyl acetate gave the title compound as a white solid (1.15 g). Mp 140–142° C.; TLC (dichloromethane/methanol 30:0.4): Rf=0.60. $^1$H NMR ($CDCl_3$) δ 7.45 (s, 2H), 4.65 (br s, 2H), 4.05 (s, 2H), 4.00 (s, 1H), 1.40 (s, 9H). Anal. calcd. for $C_{11}H_{16}N_2O_2SBr_2$: C, 33.02; H, 4.03; N, 7.00. Found: C, 33.52; H, 4.04; N, 6.92.

Preparation 5

4-t-Butylaminosulphonylmethyl-2,6-dibromo-N-trifluoroacetylaniline

To a stirred solution of the product of Preparation 4 (1.01 g, 2.52 mmol) and pyridine (0.26 mL, 3.28 mmol, 1.30 eq) in anhydrous methylene chloride (15 mL) at 0° C. under a nitrogen atmosphere was added dropwise trifluoroacetic anhydride (0.38 ml, 2.68 mmol, 1.1 eq). The resultant reaction mixture was stirred at 0° C., under a nitrogen atmosphere, for 1 hour. The reaction mixture was then diluted with dichloromethane (150 mL), washed with water (2×50 mL) and dried ($MgSO_4$). Evaporation under reduced pressure gave a white solid which was recrystallized from hexane/diethyl ether to give the title compound as a white solid (1.10 g). mp 166–167° C.; TLC (dichloromethane/methanol 30:0.4): Rf=0.21. $^1$H NMR ($CDCl_3$) δ 7.75 (br s, 1H), 7.70 (s, 2H), 4.20 (s, 2H), 4.10 (s, 1H), 1.45 (s, 9H). Anal calcd. for $C_{13}H_{15}N_2O_3SBr_2F_3$: C, 31.48; H, 3.05; N, 5.65. Found: C, 31.41; H, 3.11, N, 5.55.

Preparation 6

(R)-1-(N-Benzyloxycarbonylpyrrolidin-2-yl)-3-[N-(4-t-butylaminosulphonylmethyl-2,6-dibromophenyl)-N-trifluoroacetylamino]propene To a stirred solution of the product of Preparation 5 (28.0 g, 56.0 mmol) and triphenylphosphine (15.0 g, 86.0 mmol, 1.53 eq) in anhydrous tetrahydrofuran (70 mL), under a nitrogen atmosphere, at 10° C., was added dropwise a solution of diethylazodicarboxylate (8.9 mL, 56 mmol) in anhydrous tetrahydrofuran (15 mL). The reaction solution was then warmed to 25° C. and stirred for a further 25 minutes whereupon a solution of the product of Preparation 10 (14.79 g, 57.0 mmol) in anhydrous tetrahydrofuran (45 mL) was added dropwise, over 10 minutes. The reaction solution was then stirred at 25° C., under a nitrogen atmosphere for 18 hours. The resulting reaction solution was evaporated under reduced pressure, triturated with diethyl ether, filtered and the filtrate evaporated under reduced pressure and the residue was column chromatographed using silica gel (approximately 850 g), eluting with an ethyl acetate gradient in hexanes to afford the title compound as a white foam. TLC (hexane/ethyl acetate 1:1): Rf=0.65. $^1$H NMR ($CDCl_3$). [Note: due to slow nitrogen inversion two conformers of the products are seen by NMR spectroscopy] δ 7.50–7.80 (m, 2H), 7.25–7.42 (m, 5H), 5.42–5.65 (m, 2H), 5.30 (s, 0.14H), 5.00–5.20 (m, 2H), 4.02–4.55 (m, 6H), 3.28–3.45 (m, 2H), 1.25–1.90 (m, 13H). Anal calcd for $C_{28}H_{32}N_3O_5SBr_2F_3$. 7/100 $CH_2Cl_2$: C, 45.23; H, 4.34; N, 5.64. Found: C, 45.06; H, 4.44; N, 5.87.

Preparation 7

(R)-3-(N-Benzyloxycarbonylpyrrolidin-2-ylmethyl)-7-bromo-5-(t-butylaminosulphonylmethyl)-1H-indole To a stirred solution of the product of Preparation 6 (29.90 g, 40.44 mmol) in 1,2-dimethoxyethane (160 mL) under a nitrogen atmosphere at 20° C. was added palladium (II) acetate (0.97 g, 4.32 mmol) followed by tetrabutylammonium chloride hydrate (11.25 g, 40.48 mmol) and triethylamine (22.3 mL, 160 mmol). The reaction solution was stirred for a further hour at 20° C. and then heated at reflux for 18 hours. The reaction solution was then allowed to cool to 20° C., evaporated under reduced pressure, taken up in ethyl acetate (800 mL) and washed with water. The organic layer was separated, dried ($MgSO_4$) and evaporated under reduced pressure to give a dark brown foam. Column chromatography using elution with 10% acetone in dichloromethane failed to provide a more pure title compound. The resulting crude product (21.3 g of an off-white foam) was used as such in Preparation 8.

Preparation 8

(R)-7-Bromo-5-(t-butylaminosulphonylmethyl)-3-(N-methylpyrrolidin-2-ylmethyl)-1H-indole To a stirred suspension of lithium aluminium hydride (7.07 g, 186 mmol) in anhydrous tetrahydrofuran (100 mL), at 0° C., under a nitrogen atmosphere, was added dropwise, over 30 minutes, a solution of the product of Preparation 7 (21.3 g) in anhydrous tetrahydrofuran (100 mL). The resulting mixture was allowed to warm to room temperature and then stirred for a further 56 hours (Mitsunobu coupling reaction). The reaction was then cooled to 0° C. and cautiously treated with water (7.0 mL), followed by 15% aqueous sodium hydroxide solution (7.0 mL), and then with more water (21.0 mL). The resulting black precipitate was removed by filtration, washing with ethyl acetate. The filtrate was then washed with water, dried (MgSO$_4$) and evaporated under reduced pressure to give the crude product as a gum. This was column chromatographed using silica gel (50 g) and elution with dichloromethane/methanol (100:5) followed by dichloromethane/methanol/ammonium hydroxide (90:10:1) to afford the title compound as a white foam. TLC (dichloromethane/methanol/ammonium hydroxide (90:10:1): Rf=0.33. $^1$H NMR (CDCl$_3$) δ 8.35 (br s, 1H), 7.52 (s, 1H), 7.40 (s, 1H), 7.12 (s, 1H), 4.30 (s, 2H), 4.00 (s, 1H), 3.12–3.25 (m, 2H), 2.60–2.72 (m, 1H), 2.50–2.10 (m, 1H), 2.49 (s, 3H), 2.22–2.38 (m, 1H), 1.55–1.78 (m, 4H), 1.39 (s, 9H). [α]$^{25}$+47° c=0.1). Anal. calcd. for C$_{19}$H$_{28}$N$_3$O$_2$SBr: C, 51.59; H, 6.38; N, 9.50. Found: C, 51.84; H, 6.52; N, 9.52.

Preparation 9

(R)-5-(t-Butylaminosulphonylmethyl)-3-(N-methylpyrrolidin-2-ylmethyl)-1H-indole A solution of the product of Preparation 8 (5.79 g, 13.1 mmol) and 20% palladium hydroxide/carbon (5.7 g) was stirred under a hydrogen atmosphere (60 psi) for 24 hours. The resultant reaction mixture was filtered through a pad of CELITE (Trade Mark), washing with absolute ethanol. The combined filtrates were evaporated under reduced pressure. The residue was taken up in a mixture of 2N sodium bicarbonate and dichloromethane. The organic layer was separated, dried (MgSO$_4$) and evaporated under reduced pressure. This was column chromatographed using silica gel (90 g) and elution with dichloromethane/methanol/ammonium hydroxide (90:10:1) to afford the title compound as a white solid (3.0 g), mp 73–75° C. TLC (dichloromethane/methanol/ammonium hydroxide 90:10:1): Rf=0.36. $^1$H NMR (CDCl$_3$) δ 8.25 (br s, 1H), 7.60 (s, 1H). 7.35 (d, 1H), 7.22 (d, 1H), 7.05 (s, 1H), 5.25 (s, 1/5H), 4.35 (s, 2H), 3.90 (s, 1H), 3.10–3.22 (m, 2H), 2.55–2.70 (m, 1H), 2.42–2.55 (m, 1H), 2.45 (s, 3H), 2.18–2.30 (m, 1H), 1.50–1.90 (m, 4H), 1.40 (s, 9H). [α]$^{25}$=58° (CH$_3$OH, c=0.1). Anal. for C$_{19}$H$_{29}$N$_3$O$_2$S.1/10 CH$_2$Cl$_2$: C, 61.68; H, 7.91; N, 11.29. Found: C, 61.67; H, 8.14; N, 11.30.

Preparation 10

(R)-1-(N-Benzyloxycarbonylpyrrolodin-2-yl)-3-hydroxypropene

To a stirred solution of (R)-ethyl 3-(N-benzyloxycarbonylpyrrolidin-2-yl)-2-propenoate (see WO-A-92/06973, Example 13A) (10.00 mmol) in anhydrous tetrahydrofuran (75 mL) at −78° C. under nitrogen was added dropwise a solution of diisobutylaluminium hydride (1.0 M in hexanes, 12.0 mL, 22.0 mmol, 2.2 eq). The resulting solution was stirred at −78° C. under nitrogen for 30 minutes. The reaction solution was then allowed to warm to room temperature over the course of 2 hours. A saturated solution of sodium hydrogen carbonate (50 mL) was added, and the aqueous mixture was extracted with ethyl acetate (3×50 mL). The extracts were combined, dried (MgSO$_4$), and evaporated under reduced pressure. Column chromatography of the residue with diethyl ether/hexanes [1:1] afforded the title compound as a clear, colorless oil: $^1$H NMR (CDCl$_3$) δ 7.40–7.25 (m, 5H), 5.75–5.53 (m, 2H), 5.20–5.00 (m, 2H), 4.38 (br m, 1H), 4.06 (br d, J=13.7 Hz, 2H), 3.45 (br t, J=7.0 Hz, 1H), 2.03–1.68 (m, 4H); [α]$^{25}$=+34° (MeOH, c=1.0); HRMS: calculated for C$_{15}$H$_{19}$NO$_3$ 261.1365, found 261.1356.

The (R)-N-Carbobenzyloxypyrrolidine-2-carboxaldehyde starting material used in the said Example 13(A) was prepared as described for example in Tetrahedron Letters, Vol. 33, No. 52, p.p. 8011–8014, 1992. It can also be prepared as described by Nishikata et. al. in Chem. Pharm. Bull., 34(7), 2931–2936 (1986).

EXAMPLE 1

(R)-5-(Aminosulphonylmethyl)-3-(N-methylpyrrolidin-2-ylmethyl)-1H-indole

A solution of the product of Preparation 9 (5.92 g, 16.3 mmol) and p-toluenesulphonic acid (470 mg, 2.5 mmol) in acetic anhydride (:90 mL) was refluxed, under a nitrogen atmosphere, for 6 hours. The reaction mixture was then cooled to 25° C. and evaporated under reduced pressure, azeotroping with toluene and dichloromethane. The resultant dark brown foam was dissolved in trifluoroacetic acid (50.0 mL) and stirred under a nitrogen atmosphere at 25° C. for 18 hours. The reaction mixture was then evaporated under reduced pressure, azeotroping with dichloromethane. A slurry of potassium carbonate (1.86 g) in methanol (85 mL) was added to the resultant gum and the reaction mixture heated to reflux for 30 minutes. The resultant reaction mixture was then cooled to 25° C. and evaporated under reduced pressure to give a black oil, Purification by column chromatography using silica gel and elution with methylene chloridelmethanol/ammonium hydroxide 90:10:1) afford the title compound as a white foam (2.6 g). TLC (dichloromethane/methanol/ammonium hydroxide 80:20:1): Rf=0.43. $^1$H NMR (CD$_3$OD) δ 7.62 (s, 1H), 7.35 (d, 1H), 7.18 (d, 1H), 7.10 (s, 1H), 5.48 (s, 9/10H), 4.40 (s, 2H), 3.08–3.30 (m, 2H), 2.55–2.70 (m, 2H), 2.50 (s, 3H), 2.20–2.42 (m, 1H), 1.52–1.90 (m, 4H). [α]$^{25}$=65° (CH$_3$OH, c:=0.1) Anal. calcd. for C$_{15}$H$_{21}$N$_3$SO$_2$ 9/20 CH$_2$Cl$_2$: C, 53.69; H, 6.39; N, 12.16. Found: C, 53.58; H, 6.45; N, 11.76.

We claim:

1. (R)-5-(Aminosulphonylmethyl)-3-(N-methylpyrrolidin-2-ylmethyl)-1H-indole and its pharmaceutically acceptable salts.

2. A pharmaceutical composition comprising (R)-5-(aminosulphonylmethyl)-3-(N-methylpyrrolidin-2-ylmethyl)-1H-indole or a pharmaceutically acceptable salt thereof and a pharmaceutically acceptable dilutent or carrier.

3. A pharmaceutical composition for oral, parental, sublingual or buccal administration comprising an amount of the compound of claim 1 or a pharmaceutically acceptable salt thereof ranging from 0.1 μg to less than 0.1 mg and a pharmaceutically acceptable diluent or carrier.

4. A pharmaceutical composition for oral, parental, sublingual or buccal administration comprising an amount of the compound of claim 1 or a pharmaceutically acceptable salt thereof ranging from 0.1 μg to 0.09 mg and a pharmaceutically acceptable diluent or carrier.

5. A pharmaceutical composition for oral, parental, sublingual or buccal administration comprising an amount of the compound of claim 1 or a pharmaceutically acceptable salt thereof ranging from 0.5 μg to 0.09 mg and a pharmaceutically acceptable diluent or carrier.

6. A pharmaceutical composition according to claim 2 which is in the form of a tablet, capsule, or unit dose for injection.

7. A pharmaceutical composition for aerosol administration comprising an amount of the compound of claim 1 or a pharmaceutically acceptable salt thereof ranging from 0.01 μg to less than 20 μg per metered dose and a pharmaceutically acceptable diluent or carrier.

8. A pharmaceutical composition for aerosol administration comprising an amount of the compound of claim 1 or a pharmaceutically acceptable salt thereof ranging from 0.01 μg to 19 μg per metered dose and a pharmaceutically acceptable diluent or carrier ingredient.

9. A pharmaceutical composition for aerosol administration comprising an amount of the compound of claim 1 or a pharmaceutically acceptable salt thereof ranging from 0.05 μg to 19 μg per metered dose and a pharmaceutically acceptable diluent or carrier.

10. (R)-5-(aminosulphonylmethyl)-3-(N-methylpyrrolidin-2-ylmethyl)-1H-indole.

11. A pharmaceutical composition for treating disorders arising from deficient serotonergic neurotransmission comprising an amount of a compound according to claim 1 effective in treating such a disorder and a pharmaceutically acceptable carrier.

12. A pharmaceutical composition for treating a condition selected from depression, anxiety, eating disorders, obesity, drug abuse, cluster headache, migraine, pain, chronic paroxysmal hemicrania and headache associated with vascular disorders comprising an amount of a compound according to claim 1 effective in treating such condition and a pharmaceutically acceptable carrier.

13. A method for treating a condition selected from hypertension, depression, anxiety, bating disorders, obesity, drug abuse, cluster headache, migraine, pain and chronic paroxysmal hemicrania and headache associated with vascular disorders comprising administering to a mammal requiring such treatment an amount of a compound according to claim 1 effective in treating such condition.

14. A method for treating disorders arising from deficient serotonergic neurotransmission comprising administering to a mammal requiring such treatment an amount of compound according to claim 1 effective in treating such a disorder.

* * * * *